US011036352B2

(12) United States Patent
Yamane et al.

(10) Patent No.: US 11,036,352 B2
(45) Date of Patent: Jun. 15, 2021

(54) INFORMATION PROCESSING APPARATUS AND INFORMATION PROCESSING METHOD WITH DISPLAY OF RELATIONSHIP ICON

(71) Applicant: CANON KABUSHIKI KAISHA, Tokyo (JP)

(72) Inventors: Toshimizu Yamane, Tokyo (JP); Yoshio Iizuka, Takatsuki (JP); Gakuto Aoyama, Kyoto (JP); Kazuhito Oka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/995,729

(22) Filed: Jun. 1, 2018

(65) Prior Publication Data
US 2018/0356958 A1     Dec. 13, 2018

(30) Foreign Application Priority Data
Jun. 9, 2017    (JP) .............................. JP2017-114689

(51) Int. Cl.
*G06F 17/00*      (2019.01)
*G06F 3/0481*     (2013.01)
(Continued)

(52) U.S. Cl.
CPC .......... *G06F 3/04817* (2013.01); *A61B 5/743* (2013.01); *A61B 5/7435* (2013.01);
(Continued)

(58) Field of Classification Search
CPC .. G06F 3/04817; G06F 16/2453; G06F 16/30; G06F 3/0482; G06F 3/0484; A61B 5/7435; A61B 5/743; A61B 5/0013
(Continued)

(56) References Cited

U.S. PATENT DOCUMENTS 7,158,971 B1 *   1/2007   Bascom .............. G06F 17/2247
8,943,441 B1 *   1/2015   Patrick ................. G06F 3/0484
                                                                                                                                           715/853

(Continued)

FOREIGN PATENT DOCUMENTS

JP      2007-075158      3/2007
JP      2007-233841      9/2007
(Continued)

OTHER PUBLICATIONS

Office Action dated Jan. 5, 2021 in counterpart Japanese Application No. 2017-114689, together with English translation thereof.

*Primary Examiner* — Jason T Edwards
(74) *Attorney, Agent, or Firm* — Venable LLP

(57) ABSTRACT

The present invention has an objective to display information more suitable for searching for medical information. An information processing apparatus includes a display control unit configured to display, when a first medical information item included in a plurality of medical information items is associated with a second medical information item, an icon indicating that a medical information item related to the first medical information item is present, on a display unit in conjunction with a thumbnail of the first medical information item, wherein the display control unit performs, when the icon is selected, such control as to display a display information item indicating a relationship between the first medical information item and the second medical information item, on the display unit.

20 Claims, 14 Drawing Sheets

(51) Int. Cl.
  *G06F 3/0482* (2013.01)
  *G06F 3/0484* (2013.01)
  *A61B 5/00* (2006.01)
  *G06F 16/2453* (2019.01)
  *G06F 16/30* (2019.01)
(52) U.S. Cl.
  CPC .......... *G06F 3/0482* (2013.01); *G06F 3/0484* (2013.01); *G06F 16/2453* (2019.01); *G06F 16/30* (2019.01); *A61B 5/0013* (2013.01)
(58) Field of Classification Search
  USPC ........................................................ 715/835
  See application file for complete search history.

(56) References Cited

U.S. PATENT DOCUMENTS

| | | | | |
|---|---|---|---|---|
| 9,378,569 | B2 | 6/2016 | Yamane | G06T 11/206 |
| 2003/0058275 | A1* | 3/2003 | Pilu | H04N 7/147 |
| | | | | 715/751 |
| 2003/0158850 | A1* | 8/2003 | Lawrence | G06F 16/313 |
| 2004/0267124 | A1* | 12/2004 | Roundhill | A61B 8/465 |
| | | | | 600/443 |
| 2008/0163118 | A1* | 7/2008 | Wolf | G06F 16/168 |
| | | | | 715/835 |
| 2008/0172255 | A1 | 7/2008 | Hirakawa et al. | 705/3 |
| 2009/0054755 | A1 | 2/2009 | Shiibashi | 600/407 |
| 2009/0262894 | A1* | 10/2009 | Shukla | A61N 5/1049 |
| | | | | 378/65 |
| 2009/0265106 | A1* | 10/2009 | Bearman | G06Q 10/00 |
| | | | | 701/300 |
| 2011/0125528 | A1* | 5/2011 | Padate | G06Q 50/24 |
| | | | | 705/3 |
| 2011/0126149 | A1* | 5/2011 | Lalena | G06F 19/00 |
| | | | | 715/805 |
| 2012/0229657 | A1* | 9/2012 | Calman | G06Q 50/01 |
| | | | | 348/207.1 |
| 2013/0330007 | A1* | 12/2013 | Kim | G06K 9/00671 |
| | | | | 382/195 |
| 2014/0046699 | A1 | 2/2014 | Fukatsu et al. | 705/3 |
| 2014/0112447 | A1* | 4/2014 | Semba | A61B 6/545 |
| | | | | 378/98 |
| 2014/0229872 | A1* | 8/2014 | Johnson | G06Q 10/06 |
| | | | | 715/769 |
| 2014/0280151 | A1* | 9/2014 | Micaelian | G06F 16/2465 |
| | | | | 707/737 |
| 2015/0082220 | A1* | 3/2015 | Lane | A61N 5/1039 |
| | | | | 715/771 |
| 2015/0242689 | A1* | 8/2015 | Mau | G06Q 50/01 |
| | | | | 382/190 |
| 2015/0249704 | A1* | 9/2015 | Shah | G06F 3/0481 |
| | | | | 715/734 |
| 2016/0018520 | A1* | 1/2016 | Hirai | A61B 8/5261 |
| | | | | 367/11 |
| 2016/0139749 | A1 | 5/2016 | Yamane | G06F 3/0482 |

FOREIGN PATENT DOCUMENTS

| | | |
|---|---|---|
| JP | 2012-230672 | 11/2012 |
| JP | 2013-075190 | 4/2013 |
| JP | 2015-035210 | 2/2015 |
| JP | 2015-060397 | 3/2015 |
| JP | 2017-010452 | 1/2017 |

\* cited by examiner

FIG. 8

| IMAGE | DATE | APPARATUS | AREA | REPORT ELAPSED DIFFERENCE | FACILITY | REMARKS |
|---|---|---|---|---|---|---|
|  | 2012/ 9/10 | PROCEDURE /MEDICATION ORDER |  |  | SHIMOMARUKO CLINIC |  |
|  | 2012/ 9/10 | READ PATHOLOGY REPORT | ABDOMEN |  | OTAKU CENTRAL HOSPITAL |  |
|  | 2013/ 2/15 | CT |  |  | SHIMOMARUKO CLINIC |  |
|  | 2013/ 2/15 | DIGITAL CAMERA /SCANNER | ABDOMEN |  | SHIMOMARUKO CLINIC |  |
|  | 2013/ 6/24 | CT |  | DIFFERENCE | SHIMOMARUKO CLINIC |  |
|  | 2013/ 9/02 | ELAPSED DIFFERENCE |  |  | SHIMOMARUKO CLINIC |  |
|  | 2013/ 9/02 | CHART |  |  | SHIMOMARUKO CLINIC |  |

800

802
810
801
803

INFORMATION PROCESSING APPARATUS AND INFORMATION PROCESSING METHOD WITH DISPLAY OF RELATIONSHIP ICON

BACKGROUND

Field of the Invention

The present invention relates to an information processing apparatus, an information processing method, and a medium.

Description of the Related Art

Recent years have seen the progress in sophistication and diversification of medical test equipment and methods. In clinical settings, accordingly, comprehensive decisions are required based on more various kinds of clinical information than ever before. For such needs, to support working on examination by medical practitioners smoothly and precisely, medical information systems such as an electronic chart and PACS (Picture Archiving and Communication System) have been being introduced into clinical settings. Japanese Patent Application Laid-Open No. 2017-10452 discloses a technique to display thumbnails corresponding to such a variety of medical information items in the form of a list and display, when a thumbnail corresponding to one medical information item is selected, a relationship line between thumbnails indicating a relationship between the selected medical information item and another medical information item. This technique allows medical information items to be searched for easily.

SUMMARY

An information processing apparatus according to one aspect of the present invention includes a display control unit configured to display, when a first medical information item included in a plurality of medical information items is associated with a second medical information item, an icon indicating that a medical information item related to the first medical information item is present, on a display unit in conjunction with a thumbnail of the first medical information item, wherein the display control unit performs, when the icon is selected, such control as to display a display information item indicating a relationship between the first medical information item and the second medical information item, on the display unit.

According to the present invention, it is possible to display information more suitable for searching for medical information.

Further features of the present invention will become apparent from the following description of exemplary embodiments with reference to the attached drawings.

BRIEF DESCRIPTION OF THE DRAWINGS

FIG. 8 is a diagram illustrating an example of the list screen.

DESCRIPTION OF THE EMBODIMENTS

Some medical information items are not associated with other medical information items. Conventional techniques have a problem in that users cannot understand whether a related medical information item is present until selecting a thumbnail.

The present invention is made in view of such a problem and has an objective to display information more suitable for searching for medical information.

Hereafter, an embodiment of the present invention will be described with reference to the accompanying drawings.

Figure 1:
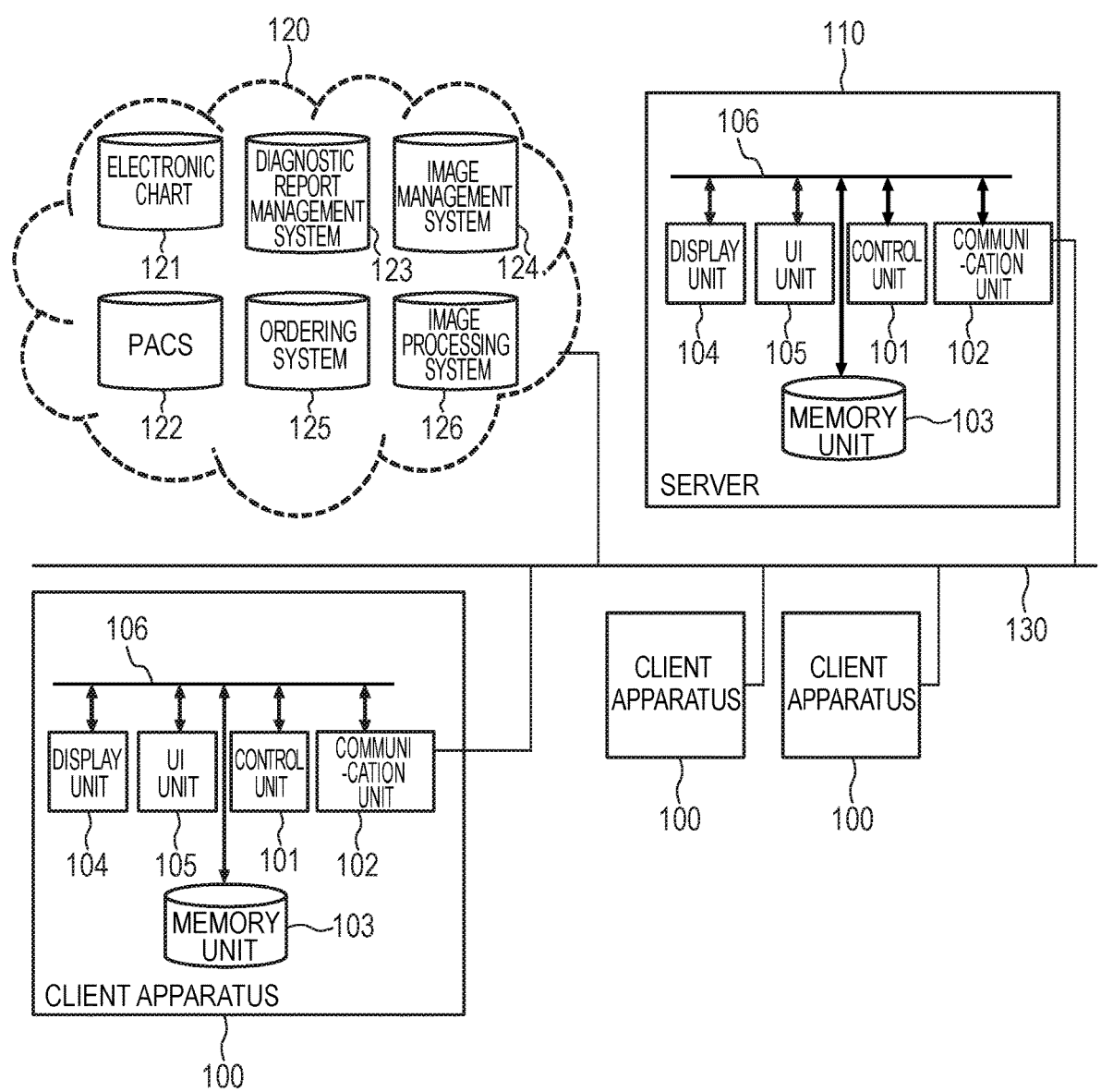
FIG. 1 is a diagram illustrating a medical system.

FIG. 1 is a diagram illustrating a medical system as an information processing system according to a first embodiment. The medical system is configured to manage medical information and display a list screen containing a plurality of medical information items in response to an operation of a user such as a medical practitioner. At this point, the medical system displays a list screen with which a user can easily grasp relations between medical information items.

The medical system includes client apparatuses 100, a server 110, and a medical information system 120. In an example illustrated in FIG. 1, three client apparatuses 100 are illustrated, but the number of client apparatuses 100 included in the medical system is not limited to the embodiment. The client apparatuses 100 are an example of information processing apparatuses used by users such as medical practitioners. The client apparatuses 100 are each configured to display medical information on a patient in response to a user operation. The server 110 is configured to receive a request from a client apparatus 100, refer to the medical information system 120 as necessary, and responds to the client apparatus 100 with a request result.

The client apparatuses 100 each include a control unit 101, a communication unit 102, a memory unit 103, a display unit 104, a UI unit 105, and a connection unit 106. The control unit 101 includes a CPU and is configured to execute a process according to a program. The communication unit 102 is configured to exchange information with the outside of the apparatus. The memory unit 103 is configured to store a program and intermediate information. The display unit 104 is configured to display a processing result. The UI unit 105 is configured to inform the control unit 101 of an input from a user. The connection unit 106 is a bus or the like for connecting these units. The functions and processes of the client apparatus 100 to be described later are implemented by the control unit 101 reading and executing programs stored in the memory unit 103. The hardware configuration of the server 110 is the same as that of the client apparatus 100.

The medical information system 120 is configured to store and manage medical information. Specifically, the medical information system 120 includes an electronic chart 121 and a PACS (Picture Archiving and Communication System) 122. The medical information system 120 further includes a diagnostic report management system 123, an image management system 124, an ordering system 125, and an image processing system 126. The electronic chart 121 is configured to manage patient basic information (name, sex, date of birth, insurance information, etc.) and chart notes (progress notes). The PACS 122 is configured to manage DICOM images such as CTs/MRIs. The diagnostic report management system 123 is configured to manage interpret reports and pathology reports. The image management system 124 is configured to manage images other than DICOM (camera pictures and scanned documents). The ordering system 125 is configured to manage instructions of medication or treatment.

The image processing system 126 performs image processing on a medical image obtained through a medical test (medical test image) to produce an image useful for diagnosis (hereafter, this will be referred to as a derived image) and stores the image in the PACS 122 and the image management system 124. Here, derived images include typical one produced based on a plurality of medical test images (hereafter, this will be referred to as a comparison image). The comparison image is an image referred to when a plurality of medical test images are compared with one another. The comparison image is produced through image processing to compare the plurality of medical test images with one another (comparison process). Examples of the comparison image include a difference image indicating a difference between two medical test images and a fusion image synthesized by superimposing two medical test images. A derived image itself is used in some cases as an input for other image processing and is desirably treated the same as a medical test image without special distinction. A network 130 connects these apparatuses.

Medical test images such as CTs/MRIs includes a plurality of axial images, and images including the plurality of axial images will be collectively referred to one medical information item. Derived images such as comparison images produced by the image processing system 126 similarly include a plurality of axial images, and images including the plurality of axial images will be collectively referred to one medical information item.

A client apparatus 100 refers to the medical information system 120 via the server 110 or directly, not via server 110. Meanwhile, the server 110 may simply relay a request from a client apparatus 100 to the medical information system 120. The server 110 may also partially bear a process performed by the client apparatus 100. The server 110 may also perform a function of analyzing a medical image or an additional serves such as an information adding function.

The medical information system 120 may be structured on the Internet as a medical information cloud. The cloud (or cloud computing) is a usage of computer resources based on a network, especially the Internet. In this case, the medical information system 120 may collectively manage medical information items of a plurality of hospitals. The medical information system 120 may share medical information among a contracted hospital group led by an insurance company, a hospital group of a medical corporation or at a national level.

The network 130 may be an intranet operated within a hospital or an organization, or the Internet. The network 130 may be a wireless connection such as WiFi (IEEE 802.11 series) and a wide-area cellular network (3G or LTE).

Figure 2:
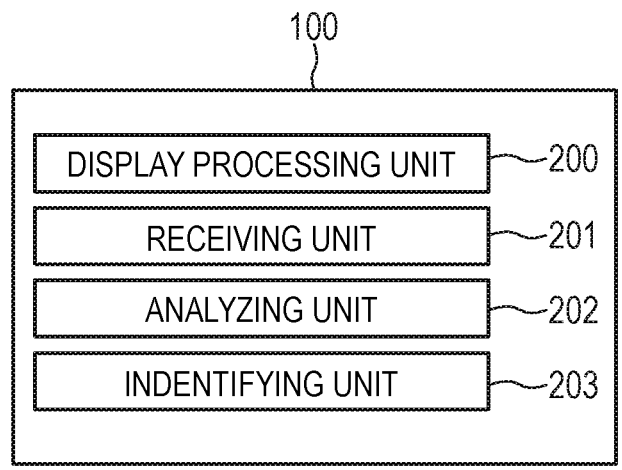
FIG. 2 is a diagram illustrating a functional configuration of a client apparatus.

FIG. 2 is a diagram illustrating a functional configuration of a client apparatus 100. The client apparatus 100 includes a display processing unit 200, a receiving unit 201, an analyzing unit 202, and an identifying unit 203. The display processing unit 200 is configured to display various kinds of information on the display unit 104. The receiving unit 201 is configured to receive various kinds of instructions via the UI unit 105. The analyzing unit 202 is configured to analyze medical information obtained from the medical information system 120 via the receiving unit 201. The identifying unit 203 is configured to identify one or more of additional medical information items having a predetermined relationship with a medical information item. The relationship will be described later in detail.

As another example, the functions of the client apparatus 100 may be implemented using a processor other than the CPU. For example, in place of the CPU, a GPU (Graphics Processing Unit) may be used. As still other examples, each of the functions of the client apparatus 100 illustrated in FIG. 2 may be implemented by a plurality of CPUs, ROMs, RAMs, and the like ganged together, or may be implemented by a hardware circuit.

Figure 3:
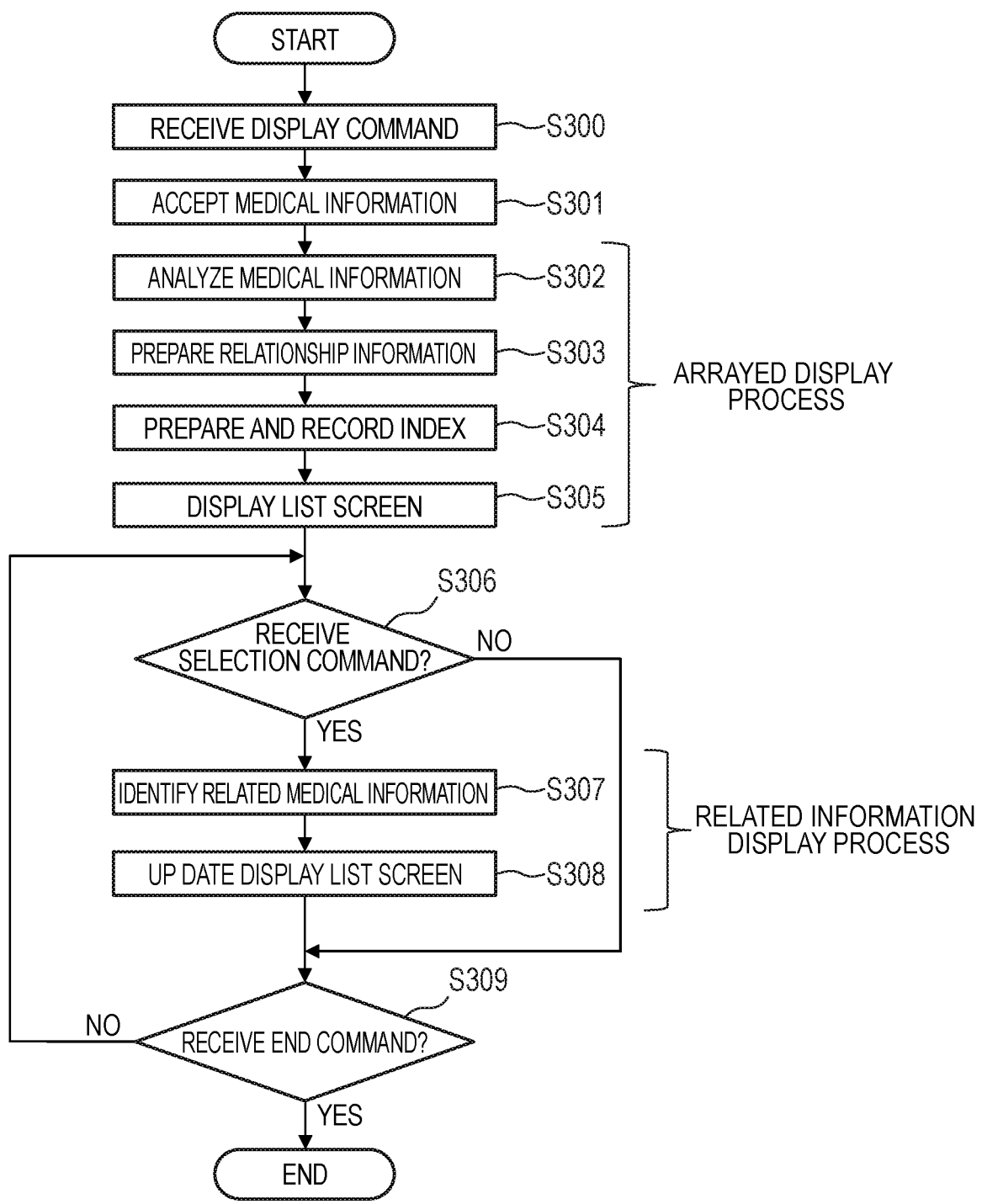
FIG. 3 is a flowchart illustrating a display process.

FIG. 3 is a flowchart illustrating a display process by a client apparatus 100. A medical information display process includes a display command receiving process, a medical information accepting process, an arrayed display process, and a related information display process. The display command receiving process is a process for starting various processes of the client apparatus 100. The medical information accepting process is a process for accepting medical information on a patient held in the medical information system 120 via the server 110. The arrayed display process is a process for analyze the accepted medical information on the patient and performing arrayed display appropriately. The related information display process is a process for presenting a relationship between medical information items in arrayed display, to a user in an understandable manner. The processes will be each described below in detail with reference to the flowchart. Note that, as a precondition of the medical information display process, the control unit 101 is supposed to read setting information from nonvolatile memory device or over the network 130, on start-up of a client apparatus 100. The setting information contains factory default values or user designated values set with a tool separately.

In S300, in response to a user operation or over the network 130, the receiving unit 201 receives a display command for a list screen of medical information in which a patient is specified by a patient ID for identifying the patient. For example, when a user uses the UI unit 105 to select a known patient number (patient ID) or a patent name, on an input form in a graphical user interface displayed on the display unit 104, the receiving unit 201 receives the display command. For another example, when a communication message containing a patient search expression (e.g., database search expression) is received via the communication unit 102, the receiving unit 201 accepts the display command.

Next, in S301, the receiving unit 201 accepts medical information about the patient indicated in the display command from the medical information system 120 via the communication unit 102. Specifically, the receiving unit 201 accepts an electronic chart containing patient basic information (name, date of birth, sex, etc.) about the patient related to the display command, progress notes, and laboratory test information (blood test values, cancer tumor marker values, etc.) from the electronic charts 121. The receiving unit 201 further accepts, from the PACS 122, medical test images, such as CTs and MRIs, and derived images produced by the image processing system 126. The receiving unit 201 also accepts an interpret report and a pathology report from the diagnostic report management system 123. The receiving unit 201 further accepts a camera image and a scanned image from the image management system 124. The receiving unit 201 further accepts medication information from the ordering system 125. The receiving unit 201 may further accept patient additional information such as contraindications, insurance information, and hospitalization information from the medical information system 120 (e.g., the electronic chart 121), as necessary. Here, the electronic chart, the medical test images, the derived images, the interpret report, the pathology report, the camera image, the scanned image, the medication information, and the patient additional information are all examples of the medical information.

Next, in S302, the analyzing unit 202 analyzes the medical information accepted in S301. Specifically, the analyzing unit 202 extracts date-and-time information, type information, area information, attending medical practitioner information, a representative image, various kinds of attribute information from each of the medical information items. Here, the date-and-time information refers to a medical test/measurement date and time of a medical test such as CT/MRI, a date and time of a subject medical test of an interpret report, filling-out date and time of a progress note, and a date and time of a conference, a date and time of producing a derived image. The representative image is an image depicting the medical information. When the medical information is in the form of an image, the medical information contains a plurality of medical images, and the representative image is an image representatively showing this plurality of medical images. In the medical information system 120, a representative image is supposed to be set beforehand for each medical information item. In the medical information system 120, for one medical image, a plurality of representative images are supposed to be set with their priorities. The analyzing unit 202 analyzes information items contained in the medical information itself, link information and refer information contained in the attribute information of the medical information, to extract the above kinds of information. Examples of the attribute information include an Accession Number of a DICOM image, various kinds of UID, a test order number of a blood test, and a document reference number of the minutes of a conference.

Next, in S303, the analyzing unit 202 refers to the analyzing results of S302. Then, considering the medical information items obtained in S301 to be processed, the analyzing unit 202 specifies another medical information item having a predetermined relationship with the medical information item to be processed. Based on the relationship between the specified medical information items, the analyzing unit 202 then creates relationship information and records the created relationship information in the control unit 101 serving as a memory unit, or the memory unit 103.

Here, the relationship and the relationship information will be described. Examples of the predetermined relationship include a diagnosis basis relationship, a medication decision relationship, a citation/aggregation relationship, and a causal relationship between medical test images. The diagnosis basis relationship is a relationship between an interpret report and a DICOM image, such as CT and MRI, or ROI (Region Of Interest) information providing a basis for a diagnosis in the interpret report. The medication decision relationship is a relationship between a medication order and a medication potency, a blood test value, a cancer tumor marker value, a contraindication information item referred to in the medication order. The citation/aggregation relationship is a relationship between an electronic chart and pictures of an affected part before and after a surgery, the minutes of a preoperative conference, and a postoperative course note cited in a summary of operation in the electronic chart. The causal relationship between medical test images is a relationship between an original medical test image and a derived image generated from the original medical test image by image processing performed by the image processing system 126. The information items related these relationships are all assumed to be identifiable from medical information or the attribute information of the medical information.

The relationship information is information indicating an identified relationship and medical information items related to the relationship. For example, assume that a medical information item A (interpret report) is diagnostically based on a medical information item B (a CT medical test image) and a medical information item C (an MM medical test image). In this case, the analyzing unit 202 produces a relationship information item indicating that "the medical information item A, the medical information item B, and the medical information item C have a relationship in the form of a diagnosis basis relationship". In addition, assume that a medical information item D (a comparison image) is produced from a medical information item E (a CT medical test image) and a medical information item F (a CT medical test image). In this case, the analyzing unit 202 produces a relationship information item indicating that "the medical information item D has a relationship in the form of a causal relationship in which the medical information item D has been produced from the medical information item E and the medical information item F".

The analyzing unit 202 determines the presence of the above relationship and identifies medical information having the above relationship based on information contained in the medical information to be processed itself or information identified from link information and reference information contained in the attribute information of the medical information. In particular, the medical information to be processed may be a derived image. In this case, the analyzing unit 202 identifies a medical test image being an original of the production of the derived image as a medical information item having a relationship with the derived image.

In the present embodiment, the comparison image such as a difference image is supposed to be produced by performing registration with one medical test image provided as a reference image (base image) and another medical test image provided as a floating image. To support this supposition, when the medical information to be processed is a comparison image such as a difference image, the analyzing unit 202 distinguishes a base image and a floating image to identify the two medical test images. In the present embodiment, information for identifying the base image and the floating image (Series Instance UID, etc.) is stored (e.g., in a private tag of a DICOM image) as meta information on a comparison image such as a difference image. The analyzing unit 202 then identifies a relationship and medical information items having the relationship, based on the meta information. There is a case where a client apparatus 100 has a preset rule that, for example, a medical test image more recently obtained has to be a base image in producing a comparison image. In this case, the comparison image need not have information for distinguishing the base image and the floating image, and the analyzing unit 202 may identify the base image and the floating image according to the rule. Here, attribute information, the information identified from link information or reference information contained in the attribute information, and meta information are examples of the additional information, and the process of S303 is an example of an identification process for identifying a relationship based on medical information or additional information of the medical information.

The analyzing unit 202 may further identify a weighted directed graph containing a relationship direction (reference direction) attribute and a relationship degree attribute and add the weighted directed graph to relationship information. Here, the relationship direction indicates a reference direction, being information for identifying medical test images to be a base image and a floating image. In a case of a diagnosis basis relationship, medical information on a diagnosis and information for identifying medical information serving as a basis form a relationship direction.

Next, in S304, the analyzing unit 202 records and manages the information extracted in S302, together with the medical information. Specifically, the analyzing unit 202 creates an index relating to date-and-time information, type information, and relationship information and records the index in the memory unit of the control unit 101. For another example, the analyzing unit 202 may record the index in the memory unit 103. This enables the reuse of extracted or obtained information. Here, the index is used to extract medical information with a specific, noticed item that has a specified value (or within a specified range), at high speed. This indexing is similar to a technology for DBMS (Database Management System) to enhance access processing. For example, as to indices relating to date and time, date-and-time information items on the medical information items are used as keys, and indices for accessing respective medical information items are managed in the form of a B tree. For example, as to indices relating to relationship information, medical information items themselves are used as keys, and indices for accessing other medical information items associated with the medical information items in the various relationships described above are managed in the forms of a hash table.

It may suffice for the client apparatus 100 to search medical information using a patient ID, date-and-time information, or the like associated with the medical information as a search key, and a process for searching for medical information is not limited to the embodiment.

Figure 4:
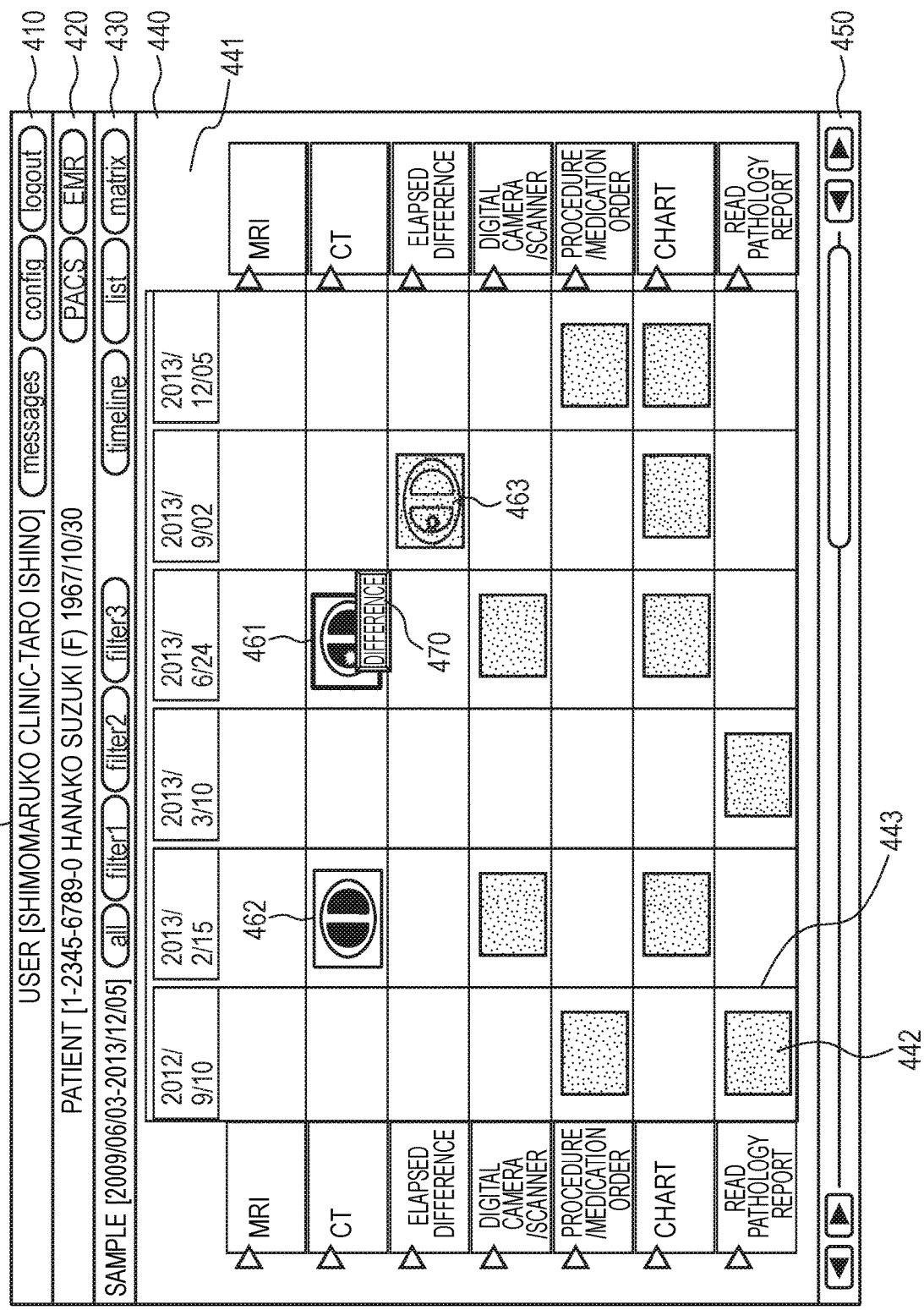
FIG. 4 is a diagram illustrating an example of a list screen.

Next, in S305, the display processing unit 200 displays a list screen of medical information items obtained in S301 based on date-and-time information items and type information items (image types) managed as indices. FIG. 4 is a diagram illustrating an example of the list screen. A list screen 400 includes a patient first area 410 displaying assigned hospital information and a user name. Furthermore, in the patient first area 410, a message display control button, a configuration button, and a logout button. In a patient second area 420, a patient name, a patient name in kana, a sex, a birth date (age), a PACS reference button, and an electronic chart reference button are displayed.

In a display control area 430, a period of obtained medical information items, a filter control button (all, filter 1, filter 2, filter 3) for narrowing medical information items to be displayed are displayed. In the display control area 430, a display style control button (timeline display, list display, matrix display) are also displayed.

In a medical information area 440, medical test type labels of medical information items are displayed in right and left parts, and date-and-time information items are displayed in an upper part. The display processing unit 200 displays a display field 441 in the medical information area 440, the display field 441 having a matrix pattern and having two orthogonal axes representing date-and-time information and type information. In the display field 441, a plurality of cells 443 are disposed in a two-dimensional manner. The display processing unit 200 disposes and displays thumbnails 442 corresponding to the respective medical information items obtained in S301 in cells 443 determined according to date-and-time information items and type information items. The display processing unit 200 displays thumbnails (reduced images) corresponding to representative images set in the respective medical information items in the cells.

In the client apparatus 100, the number of columns allowed to be disposed in a time-series direction (the horizontal direction illustrated in FIG. 4) in the display field 441, that is, the number of cells displayable in the time-series direction is supposed to be preset. Therefore, for medical information items of the same type, the number of thumbnails simultaneously displayable is limited to the preset number of cells. In the example illustrated in FIG. 4, the number of cells allowed to be disposed in the time-series direction is six. To support this limitation, if all of thumbnails to be displayed cannot be displayed simultaneously in the display field 441, the display processing unit 200 is supposed to dispose the thumbnails in a time-series order starting with the latest medical information item. The display processing unit 200 then displays thumbnails having failed to be displayed in a switching manner in response to a scroll operation.

In a range control area 450, a time scroll bar is displayed at the center, and on the right and left, two arrow buttons for movements in older/newer directions. In response to an operation of an arrow button, the display processing unit 200 is configured to display hidden columns in the display field 441. For example, in FIG. 4, when an arrow of a past direction (leftward in FIG. 4) is selected, columns move, with the result that a column of the latest date and time of Dec. 5, 2013 is no longer displayed, and a column corresponding to a date and time prior to Sep. 10, 2012 is newly displayed. Then, thumbnails corresponding to medical information items associated with this date and time are displayed in the corresponding cells.

For each of medical information items to be processed, the display processing unit 200 determines whether the each medical information item to be processed is associated with another medical information item, based on a relationship information item on the each medical information item to be processed. When the medical information item to be processed is associated with the other medical information item, the display processing unit 200 produces a relationship icon indicating the presence of a medical information item related to the medical information item to be processed. The display processing unit 200 then displays the produced relation icon in conjunction with a thumbnail of the medical information item to be processed. Specifically, the display processing unit 200 displays the relationship icon in the same cell as the cell of the thumbnail of the medical information item to be processed.

Assume that a difference image as a medical information item corresponding to a thumbnail 463 is produced from medical test images as medical information items corresponding to thumbnails 461 and 462, respectively, illustrated in FIG. 4. In addition, assume that the medical test image corresponding to the thumbnail 461 is a base image, and the medical test image corresponding to the thumbnail 462 is a floating image. In this case, the display processing unit 200 produces a relationship icon for the medical test image corresponding to the thumbnail 461 and displays a relationship icon 470 in the same cell as the cell of the thumbnail 461. At that time, as the relationship icon 470, the display processing unit 200 produces an icon indicating that the relationship is a causal relationship (difference). This enables a user to check the relationship icon 470 to grasp the presence of another medical information item having a relationship with the medical information item corresponding to the thumbnail 461 disposed in the same cell as the cell of the relationship icon 470. From the relationship icon 470, the user is further enabled to grasp that the type of the relationship is a relationship in the form of a difference causal relationship (difference).

In the present embodiment, the display processing unit 200 is configured to display a relationship icon in conjunction with the thumbnail of a base image and not to display the relationship icon on the thumbnail of a floating image. For another example, however, the display processing unit 200 may display relationship icons in conjunction with the thumbnail of a base image and the thumbnail of a floating image, respectively. In this case, the display processing unit 200 may further display relationship icons in conjunction with the respective thumbnails, the relationship icons each enabling a distinction as to whether a medical test image associated with the relationship icon is a base image or a floating image. The above process is an example of a display control process for displaying icons in conjunction with thumbnails of medical information items.

Although FIG. 4 illustrates that the relationship icon indicating a difference is displayed, the display processing unit 200 displays a relationship icon indicating another relationship similarly. For example, when a medical test image is associated with a comparison image other than a difference image or a derived image produced from a single medical test image, a relationship icon indicating a causal relationship between the medical test images is displayed. The display processing unit 200 also displays a relationship icon indicating a relationship other than a causal relationship between medical images. For example, when an interpret pathology report related to a medical test image is present, the display processing unit 200 displays a relationship icon indicating the presence (a report icon). At that time, the display processing unit 200 is desirably use relationship icons indicating the respective relationships in such a manner as to allow users to identify the relationships.

In the example illustrated in FIG. 4, thumbnails respectively indicating a procedure/medication order information item and an interpret pathology report information item are disposed in the column of Sep. 10, 2012. Similarly, thumbnails respectively indicating a CT image, a digital camera/scanner information item, and a chart information item are disposed in the column of Feb. 15, 2013. Thumbnails respectively indicating an interpret pathology report information item are disposed in the column of Mar. 10, 2013. Thumbnails respectively indicating a CT image, a digital camera/scanner information item, and a chart information item are disposed in the column of Jun. 24, 2013. In the cell of the CT image, a difference icon is disposed, the difference icon indicating that the CT image is associated with a difference image. Thumbnails respectively indicating a difference image and a chart information item are disposed in the column of Sep. 2, 2013. Thumbnails respectively indicating a procedure/medication order information item and a chart information item are disposed in the column of Dec. 5, 2013. The thumbnail of the difference image is disposed in the column of the date on which a difference image process is performed (Sep. 2, 2013).

If the medical information items obtained in S301 correspond to date-and-time information items ranging over a long period, the analyzing unit 202 may narrow medical information items to be displayed in the display field 441 based on the date-and-time information items. As seen from the above, the processes of S302 to S305 are processes equivalent to the arrayed display process.

Returning to FIG. 3, after the process of S305, in S306, the receiving unit 201 waits for a selection command to be received. For example, when a user uses a mouse cursor to focus a noticed part on the list screen 400, a selection command for a relationship icon specified by the cursor is received. The method of pointing the icon may be a known method other than using the mouse cursor. The receiving unit 201 may receive the selection command from a user interface other than the mouse cursor. When receiving the selection command (Yes in S306), the receiving unit 201 advances the process to S307. When not receiving the selection command (No in S306), the receiving unit 201 advances the process to S309.

In S307, the identifying unit 203 identifies a thumbnail in the cell in which the relationship icon is disposed and the medical information item, based on a relationship information item on the relationship information related to the selection command. Hereafter, the thumbnail in the cell in which the relationship icon related to the selection command is disposed will be referred to as a selected thumbnail, and medical information corresponding to the selected thumbnail will be referred to as selected medical information. The identifying unit 203 then refers to an index of the relationship information, identifies a medical information item having a relationship with the selected medical information item, and identifies a thumbnail corresponding to the identified medical information item. Hereafter, medical information having a relationship with selected medical information will be referred to as related medical information, and a thumbnail corresponding to related medical information will be referred to as a relation thumbnail. The related medical information is an example of medical information associated with selected medical information.

In the present embodiment, in the client apparatus 100, the indices of relationship information items are managed in the form of a hash table. The identifying unit 203 thus calculates a hash value for a selected medical information item and searches the hash table of the relationship information items using the hash value as a key. At that point, the identifying unit 203 obtains a simple relationship, as well as information on a relationship direction and a relationship degree when the relationship direction and the relationship degree are contained in the selected medical information item.

Next, in S308, the display processing unit 200 performs such control as to display information indicating a relationship between the selected thumbnail and medical information items identified from the relation thumbnail. This process is an example of the display control process. Specifically, the display processing unit 200 draws a relationship line connecting the selected thumbnail and the relation thumbnail, as the display information. In addition, the relationship may be a causal relationship between images, the causal relationship indicating that a difference image has been produced from a base image and a floating image. In this case, the display processing unit 200 displays a relation line with an arrow extending from a base image and a floating image to a difference image. This display enables a user to distinguish between the base image or the floating image and the difference image by checking the direction of the arrow.

For another example, when the relationship information contains a relationship degree attribute, the display processing unit 200 may change the thickness or color of the relationship line based on the relationship degree attribute. For example, the display processing unit 200 may display a relationship line of a larger width for a higher relationship degree. For another example, the display processing unit 200 may display a relationship line of a darker color for a higher relationship degree. For example, in a case where medical information is an interpret report, and a medical test image is determined to be important as a diagnosis basis, the relationship degree between the medical information item and the medical test image is high. The display processing unit 200 therefore may use a large with to display a relationship line extending from the interpret report when compared with a relationship line extending from another medical information item.

Figure 5:
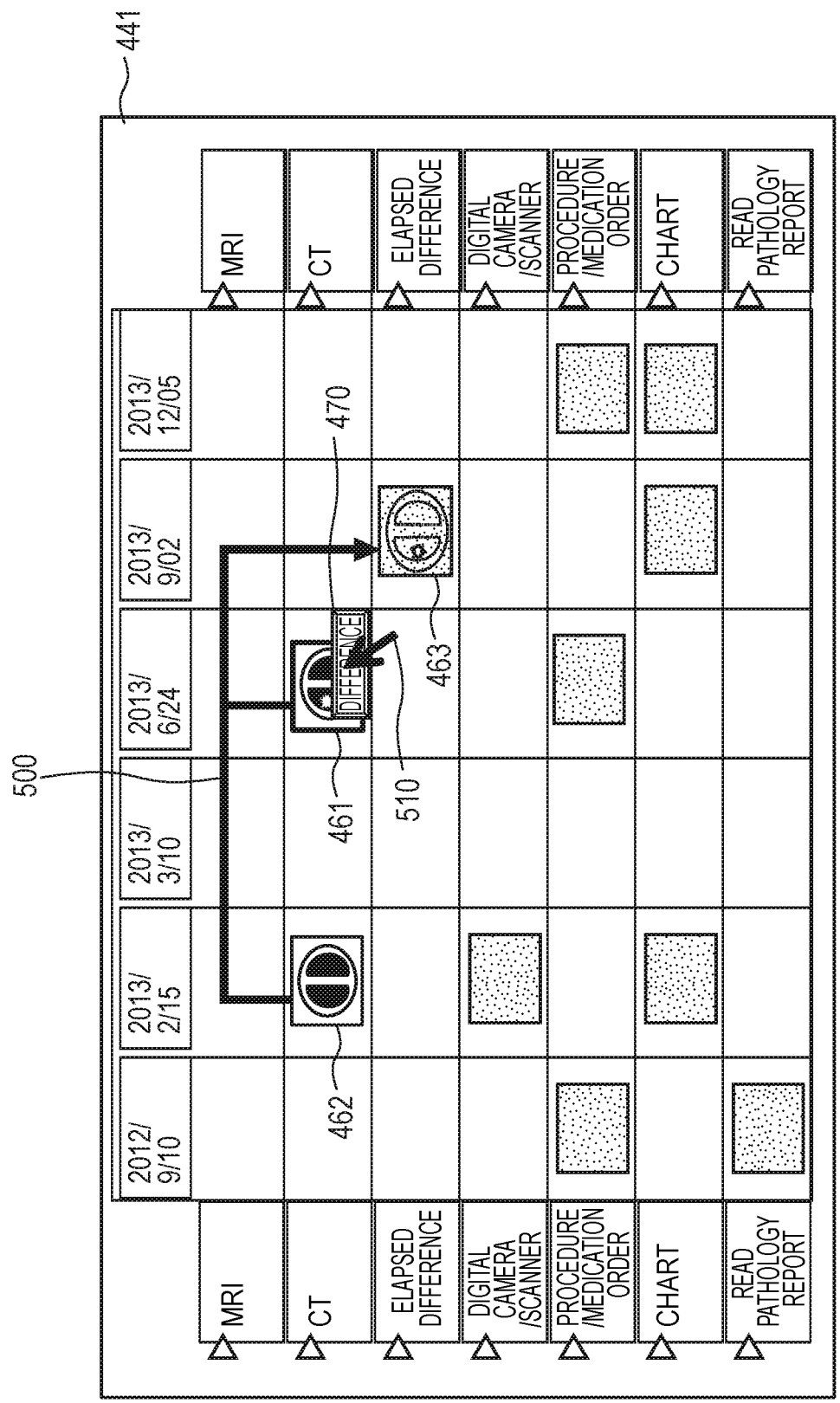
FIG. 5 is a diagram illustrating a display example of a relationship line.

FIG. 5 is a diagram illustrating a display example of a relationship line. A display field 441 illustrated in FIG. 5 corresponds to the display field 441 illustrated in FIG. 4. When a user uses a mouse pointer 510 to select a relationship icon 470, the identifying unit 203 identifies a thumbnail 461 and a medical information item corresponding to the relationship icon 470. The identifying unit 203 then identifies a medical information item corresponding to a thumbnail 462 and a medical information item corresponding to a thumbnail 463, as medical information items having difference causal relationships with the medical information item of the thumbnail 461. The display processing unit 200 then displays a relationship line 500 with an arrow extending from the thumbnails 461 and 462 to the thumbnail 463. In such a manner, medical information items having a relationship and the relationship can be grasped by selecting a relationship icon.

Returning to FIG. 3, after the process of S308, in S309, the receiving unit 201 checks for a reception of a termination command, in response to a user operation. When receiving the termination command (Yes in S309), the receiving unit 201 terminates the display process. When not receiving the termination command (No in S309), the receiving unit 201 advances the process to S306.

In such a manner, the medical system according to the present embodiment performs such control as to display a relationship icon indicating a relationship between two medical information items in conjunction with a thumbnail of a corresponding medical information item. Therefore, by checking for a relationship icon, a user can easily check for an additional medical information item having a relationship with one medical information item. When the user selects the relationship icon, the medical system performs such control as to display information indicating a relationship between a plurality of medical information items associated with the relationship icon. This display enables the user to easily grasp the relationship between the medical information items by selecting the relationship icon. As seen from the above, the medical system can display information more suitable for searching for medical information. This enables the user to easily reach materials necessary for treatment medical system from among enormous amount of medical test information items. This can also increase the efficiency of working on examination and treatment planning for busy medical practitioners.

As to a first modification of the medical system according to the first embodiment, the client apparatus 100 may dispose a thumbnail of a difference image in a column of a date of a corresponding base image or a column of a date of a floating image, rather than a column of a date on which a difference image process is performed. Alternatively, the client apparatus 100 may switch a display position of a thumbnail of a difference image from a column of a date on which a difference image process is performed, to a column of a date of a base image or a floating image, in response to a switch of a display mode.

As to a second modification, the processes to, when a relationship icon is selected, identify a relationship information item corresponding to the relationship icon and to change a displayed content are not limited to the processes of S307 and S308 described in the embodiment. That is, the client apparatus 100 may identify a relationship information item corresponding to a relationship icon, identify a plurality of medical information items and a relationship among the medical information items, indicated by the relationship information, and display a relationship line connecting the identified plurality of medical information items.

As to a third modification, a comparison image related to a relationship in the form of a causal relationship between medical information items is not limited to a difference image or a fusion image and may be any image that can be produced from a plurality of medical images. Other examples of the comparison image include a Jacobian image, which visualizes information on a local volume change in a subject occurring between two medical images to be compared. The Jacobian image can be produced by a known technique, as in producing a difference image, by nonlinear deformation registration of a plurality of medical images. Alternatively, medical information relating to a causal relationship is not limited to images and may be comparison information obtained by digitizing a result of comparing a plurality of medical information items. The comparison information may be, for example, statistical information on comparison images. For example, the comparison information may be a value obtained by quantifying the magnitude of a change between images, based on a difference image. More specifically, for example, the comparison information may be the histogram, the average value, the sum of the absolute values, or the root mean square of pixel values of a difference image, or the number of pixels having the absolute values of pixel values of a difference image greater than or equal to a threshold value.

Figure 6:
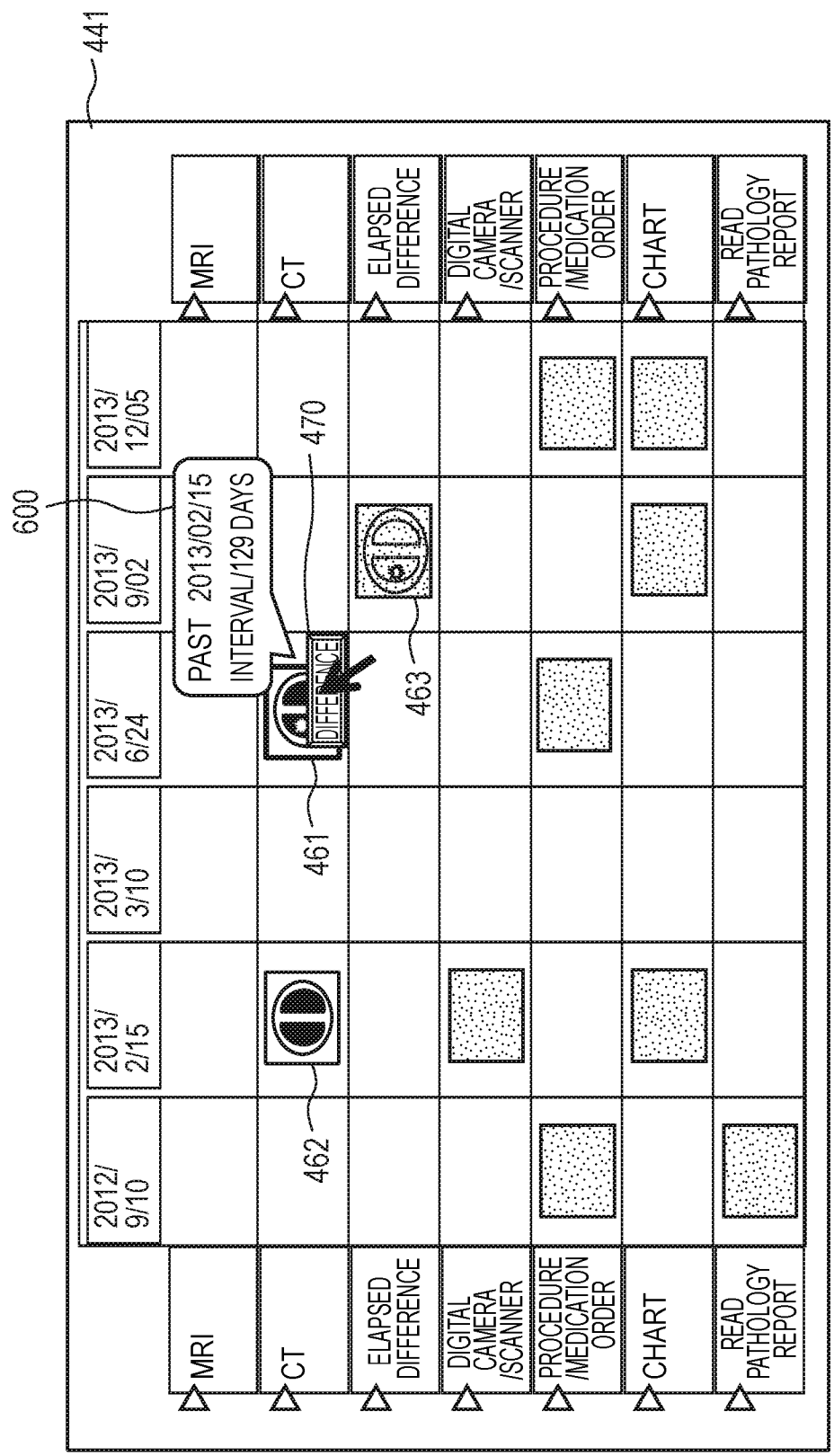
FIG. 6 is a diagram illustrating a display example of a tooltip.

As to a fourth modification, a relationship line is an example of display information indicating a relationship between medical information items, and the display information is not limited to a relationship line. For another example, when a relationship icon is selected, the display processing unit 200 may perform such control as to display a tooltip 600 as display information in conjunction with the relationship icon, as illustrated in FIG. 6. Here, the tooltip 600 includes text information indicating subtractions between dates of a plurality of medical information items having a relationship (number of days). The information included in the tooltip 600 is not limited to the number of days. The tooltip 600 is an example of display information displaying a display content in the form of text information. For another example, the tooltip 600 may include a date-and-time information item on at least one medical information item. Also in this case, the user can easily grasp the relationship between the plurality of medical information items.

For still another example, the display processing unit 200 may change thumbnails corresponding to a plurality of identified medical information items having a relationship to display forms distinguishable from other thumbnails, together with or in place of the display of a relation line. Here, the other thumbnails refer to thumbnails corresponding to one or more medical information items other than the plurality of medical information items having the relationship.

Figure 7:
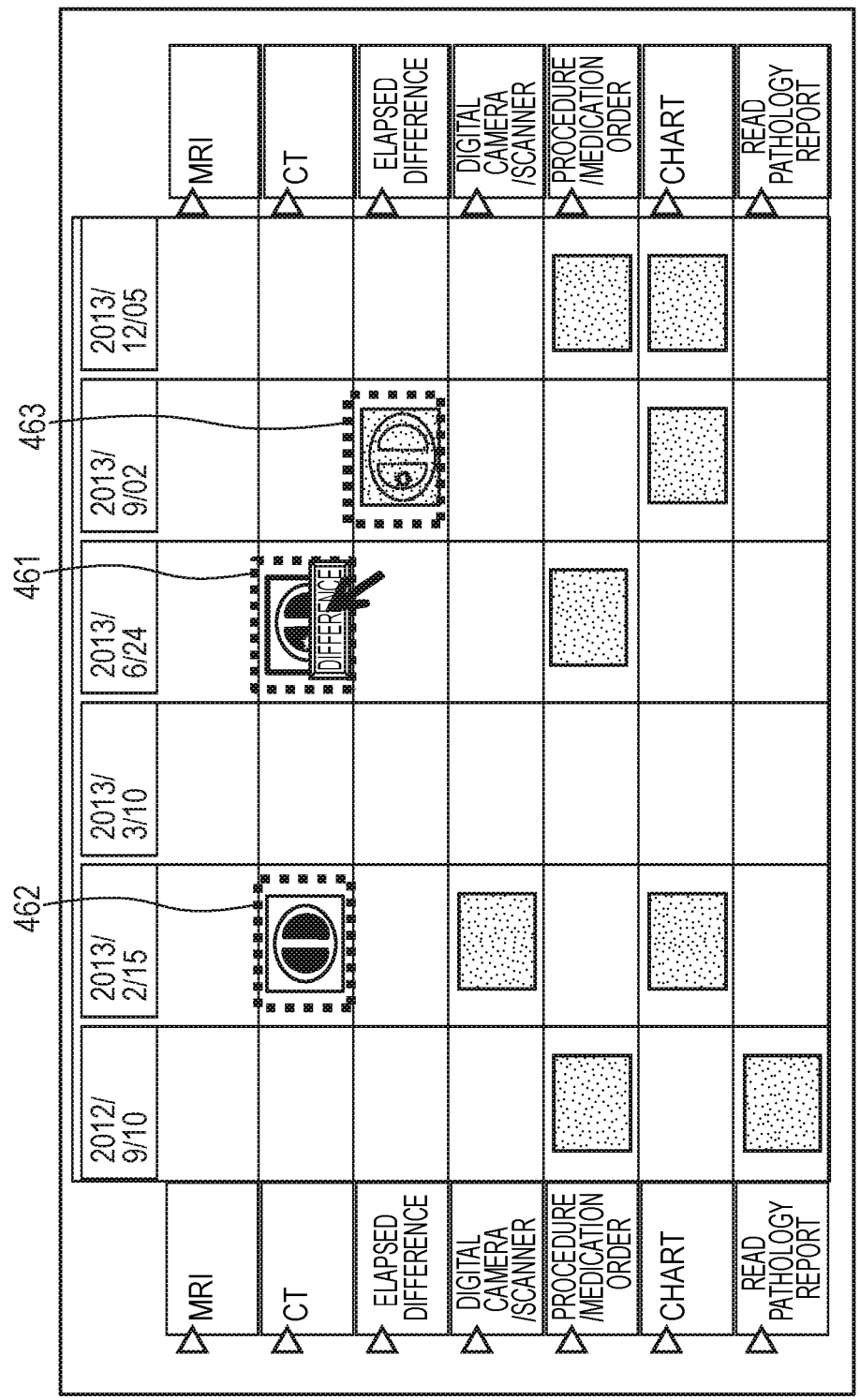
FIG. 7 is a diagram illustrating an example of highlight display.

As an example of changing display forms, as illustrated in FIG. 7, the display processing unit 200 may emphasize thumbnails corresponding to a plurality of medical information items having a relationship with highlight displays (in FIG. 7, drawn by dashed lines encircling the thumbnails). Specifically, the display processing unit 200 uses thick lines to draw the frames of thumbnails of medical information items as compared with other thumbnails. For another example, in place of the frames of thumbnails, the frames of cell in which the thumbnails are disposed may be changed. In this case, by checking for highlight displays, a user can distinguish medical information items relevant to a relation thumbnail from other medical information items. In addition, the user can grasp that medical information items relevant to highlighted thumbnails are medical information items having a relationship.

In this case, the display processing unit 200 may also change the brightness of highlight displays according to relationship degrees. A plurality of identified medical information items may differ in type from one another, as with a base image and a floating image. In this case, display forms of thumbnails corresponding to the respective identified medical information items may be changed. For example, the display processing unit 200 may change the lines of thumbnails of a base image and a floating image in thickness or color to make the base image and the floating image distinguishable from each other.

For another example of changing the display forms, the display processing unit 200 may gray out thumbnails other than thumbnails corresponding to a plurality of medical information items having a relationship. For still another example, the display processing unit 200 may decrease, relative to the matrix, the contrast of thumbnails other than thumbnails corresponding to a plurality of medical information items having a relationship. This allows for emphasizing thumbnails corresponding to a plurality of medical information items having a relationship.

As to a fifth modification, the disposition of medical information items in the list screen of medical information is not limited to the embodiment. That is, the disposition is not limited to the two-dimensional matrix disposition. In the list screen, for example, thumbnails of medical information items may be disposed in a one-dimensional manner along the date-and-time information axis, as illustrated in FIG. 8. Here, thumbnails 801 to 803 are assumed to correspond to the thumbnails 461 to 463, respectively illustrated in FIG. 5. In this example, a relationship icon 800 is disposed in the same row as the row of the thumbnail 801, and when the relationship icon 800 is selected, a relation line 810 connecting the relevant thumbnails 801, 802, and 803 is displayed.

As to a sixth modification, at least some of the processes described in the present embodiment as processes performed by the client apparatus 100 may be performed by the server 110. That is, any apparatus in the medical system may perform the processes of the display process (FIG. 3), and an entity of performing the process is not limited to the embodiment.

As to a seventh modification, a thumbnail corresponding to a comparison image or a comparison information item may be selected by a user operation. Also in this case, the client apparatus 100 may display a relationship line between the selected comparison image or comparison information item and medical information items having a relationship with the comparison image or the comparison information item. For example, when the thumbnail 463 is selected in the example illustrated in FIG. 5, the client apparatus 100 may display the relationship line 500.

As to an eighth modification, a relationship line related to a causal relationship (difference) may be any line connecting an icon of a difference image and an icon of one of two medical test images from which the difference image is produced. For another example, the relationship line related to the causal relationship (difference) may be a line connecting two medical test images from which the difference image is produced and need not connect the icon of the difference image. For example, in the example illustrated in FIG. 5, the relationship line displayed when the relationship icon 470 is selected may connect only the thumbnail 461 and the thumbnail 462 and need not connect the thumbnail 463. Alternatively the relationship line displayed when the relationship icon 470 is selected may connect only the thumbnail 461 and the thumbnail 463 and need not connect the thumbnail 462. Also in these cases, a user can grasp at least the relationship between the medical information items corresponding to the thumbnails connected by the relationship line.

Second Embodiment

Figure 9:
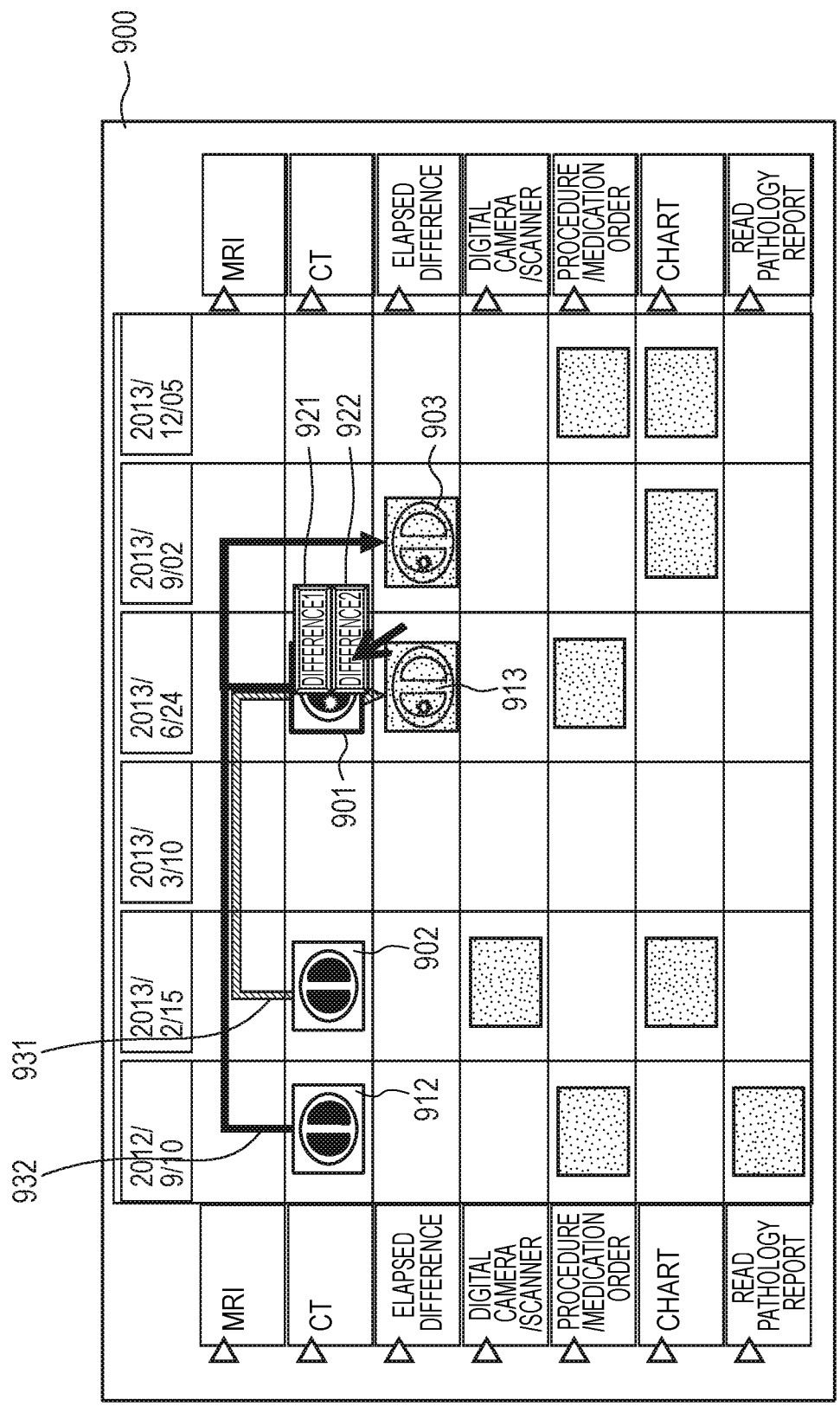
FIG. 9 is an explanatory diagram of a second embodiment.

In a medical system according to a second embodiment, when a plurality of different relationship information items are associated with one medical information item, the client apparatus 100 displays a plurality of relationship icons corresponding to the respective relationship information items in conjunction with a thumbnail of the one medical information item. FIG. 9 is a diagram illustrating an example of a display field 900. Here, medical test images as medical information items corresponding to thumbnails 901 and 902 are assumed to be images from which a difference image corresponding to a thumbnail 913 is produced. In addition, medical test images as medical information items corresponding to the thumbnail 901 and a thumbnail 902 are assumed to be images from which a difference image corresponding to a thumbnail 903 is produced. In addition, the medical test image corresponding to the thumbnail 901 is assumed to be a base image, and the medical test images corresponding to the thumbnails 902 and 912 are assumed to be floating images.

In this case, the display processing unit 200 produces two relationship icons for the medical test image corresponding to the thumbnail 901 and displays two relationship icons 921 and 922 in the same cell as the cell of the thumbnail 901. Here, the relationship icon 921 corresponds to a relationship between medical information items corresponding to the thumbnails 901, 902, and 913, respectively. The relationship icon 922 corresponds to a relationship between medical information items corresponding to the thumbnails 901, 912, and 903, respectively. When the relationship icon 921 is selected, the display processing unit 200 displays a relationship line 931 connecting the thumbnails 901, 902, and 913. When the relationship icon 922 is selected, the display processing unit 200 displays a relationship line 932 connecting the thumbnails 901, 912, and 903. The rest of the configuration and processes of the medical system according to the second embodiment are the same as the equivalent configuration and processes of the medical system according to the first embodiment.

As to a first modification of the second embodiment, when one relationship icon is selected, and the client apparatus 100 displays a relationship line corresponding to the one relationship icon, the client apparatus 100 may display a relationship line corresponding to an unselected relationship icon corresponding to the same medical information items as the medical information items of the selected relationship icon. In this case, the client apparatus 100 may display the relationship line corresponding to the unselected relationship icon in an inconspicuous manner, such as displaying the relationship line in a color lighter than the color of the relationship line corresponding to the selected relationship icon.

Figure 10:
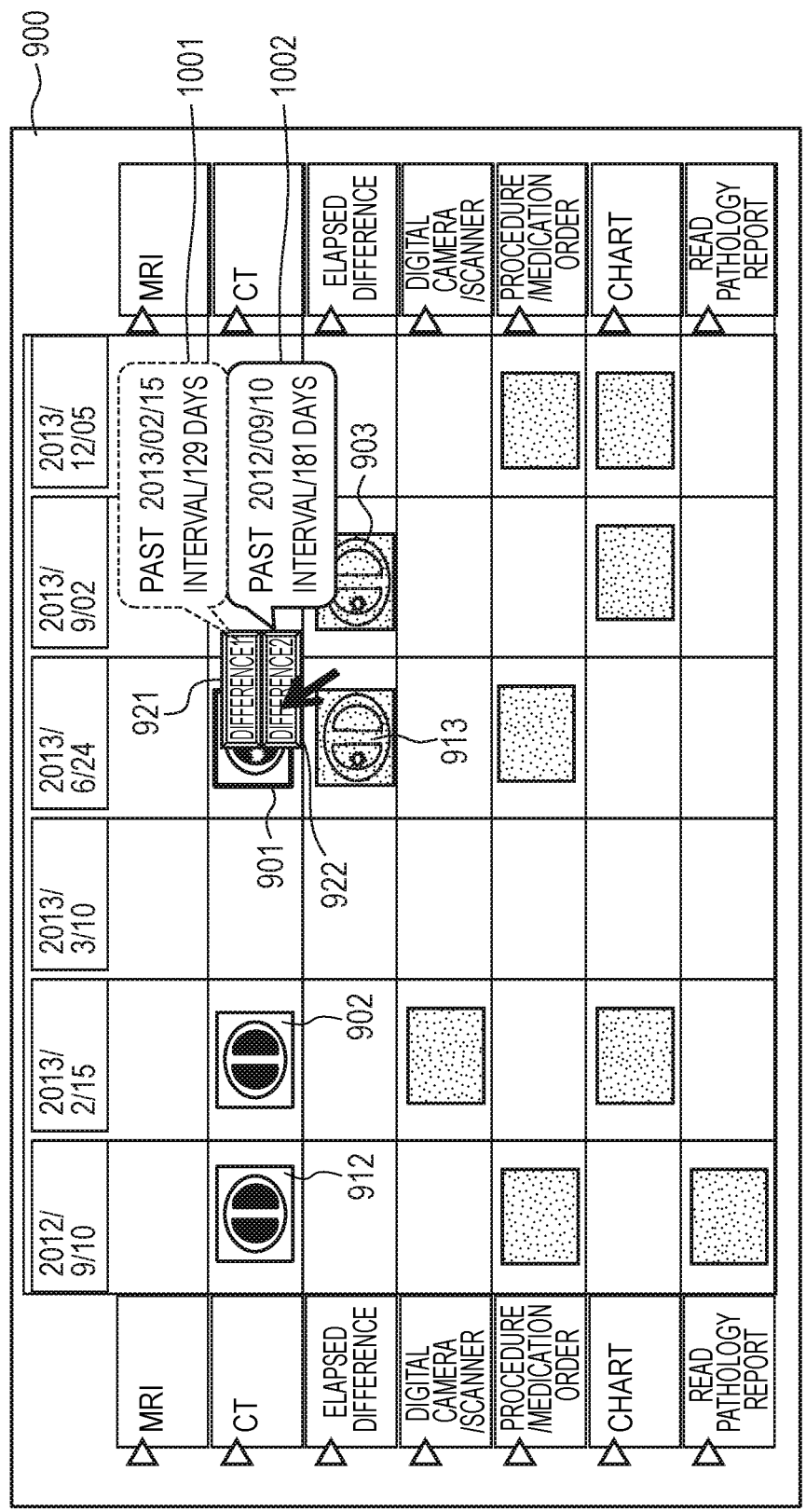
FIG. 10 is an explanatory diagram of a modification.

As to a second modification, when a relationship icon is selected, as described in the fourth modification of the first embodiment, a tooltip may be displayed as display information indicating that there is a relationship corresponding to the selected relationship icon. A display field 900 illustrated in FIG. 10 is assumed to correspond to the display field 900 illustrated in FIG. 9. When a relationship icon 921 is selected, the display processing unit 200 displays a tooltip 1001 as a display information item indicating a relationship between the medical information items corresponding to thumbnails 901, 902, and 913 in the form of text information. When a relationship icon 922 is selected, the display processing unit 200 displays a tooltip 1002 as a display information item indicating a relationship between the medical information items corresponding to thumbnails 901, 912, and 903 in the form of text information. Here, the tooltips 1001 and 1002 each include the number of days between the dates of medical test between a base image and a floating image, and a date of medical test related to the floating image.

Figure 11:
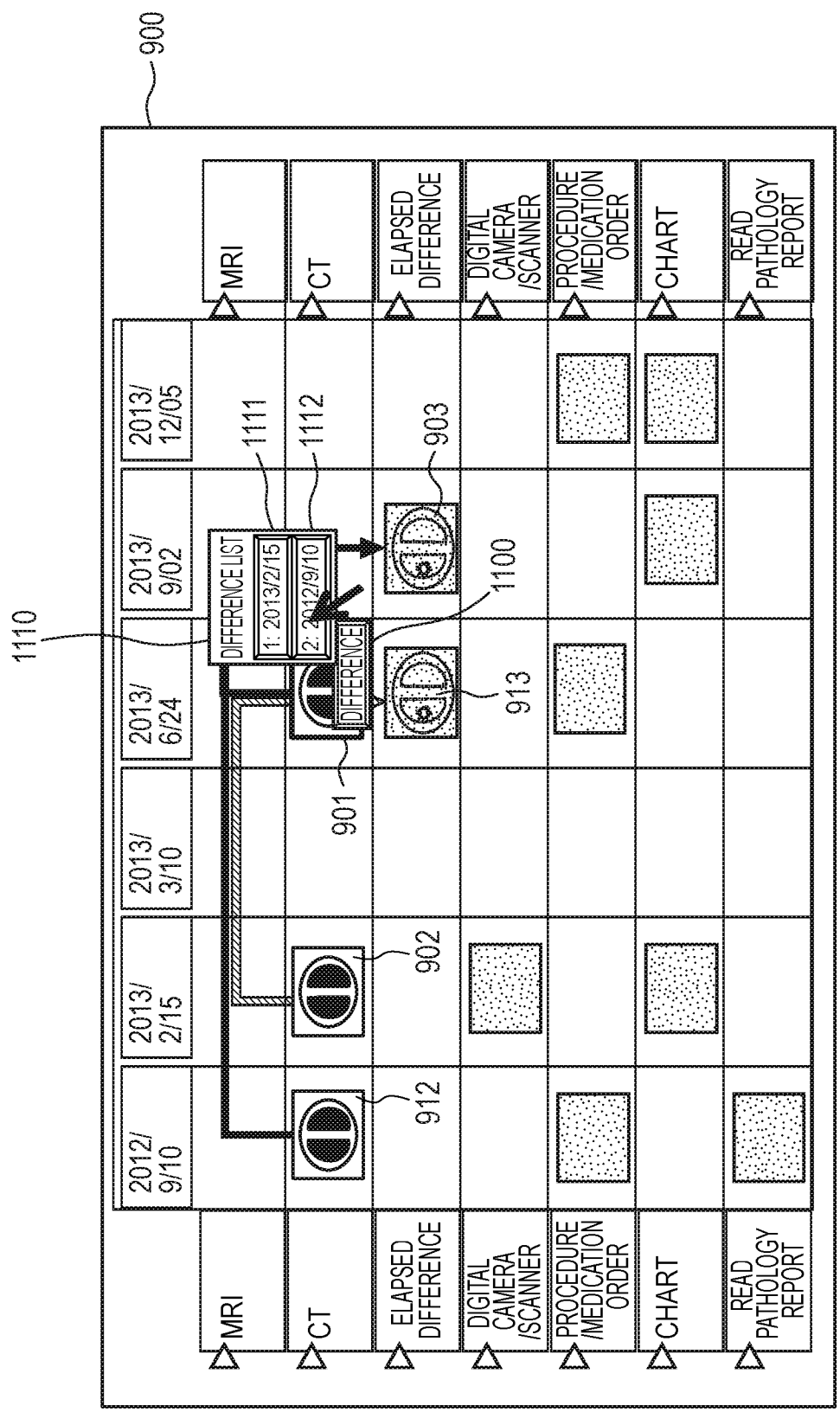
FIG. 11 is an explanatory diagram of a modification.

As to a third modification, also when a plurality of different relationship information items are associated with one medical information item, the client apparatus 100 may display only one relationship icon. When the relationship icon is selected, the client apparatus 100 may display a window displaying display information items on the plurality of relationship information items in the form of a list in conjunction with the relationship icon. FIG. 11 is a diagram illustrating a display field corresponding to the display field 900 illustrated in FIG. 9. In the example illustrated in FIG. 11, only one relationship icon 1100 is displayed in conjunction with the thumbnail 901. When the relationship icon 1100 is selected, a window 1110 is displayed. The window 1110 displays display information items 1111 and 1112 on a plurality of relationship information items. When the display information items are selected, the client apparatus 100 displays corresponding relationship lines. This display can simplify the configuration of the screen also when a large number of relationship information items are associated with one medical information item.

Figure 12:
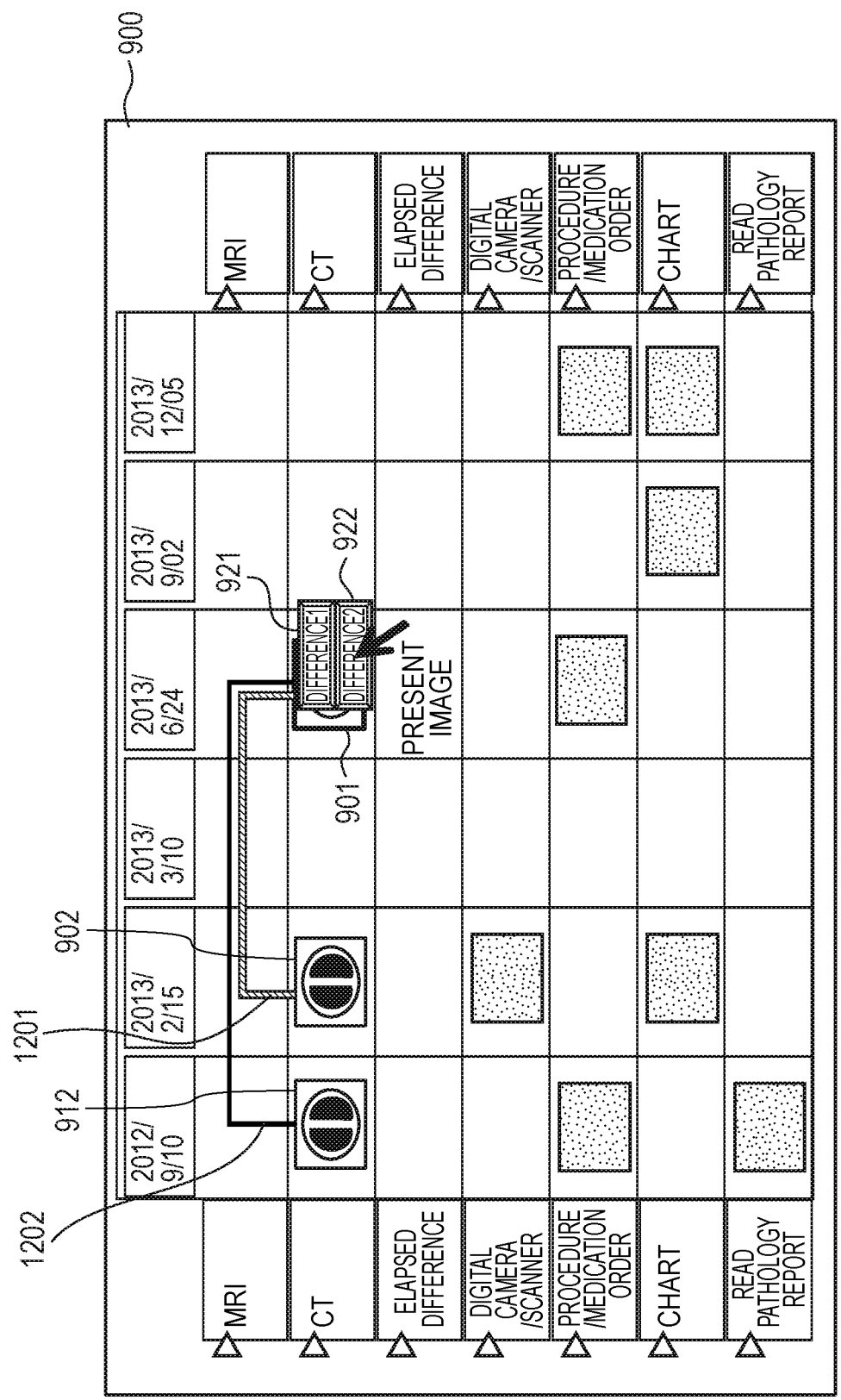
FIG. 12 is an explanatory diagram of a modification.

As to a fourth modification, the display field displays no comparison images. In this case, even when a relationship in the form of a difference causal relationship is identified, the client apparatus 100 may display a relation line connecting only thumbnails corresponding to medical test images. FIG. 12 is a diagram illustrating a display field corresponding to the display field 900 illustrated in FIG. 9. In an example illustrated in FIG. 12, when a relationship icon 921 is selected, the client apparatus 100 displays a relationship line 1201 connecting a thumbnail 901 and a thumbnail 902. When a relationship icon 922 is selected, the client apparatus 100 displays a relationship line 1202 connecting the thumbnail 901 and a thumbnail 912.

Third Embodiment

Next, description will be made of differences of a medical system according to a third embodiment from the other embodiments. In S308 described with reference to FIG. 3, when a relationship line is displayed, there is a case where at least one of a plurality of thumbnails to be connected by the relation line is not displayed in the display field due to the limitation on the number of cells in the time-series direction. In this case, to make all of the thumbnails to be connected by the relationship line displayable, the display processing unit 200 performs such control as to remove a column corresponding to at least one of thumbnails other than the thumbnails to be connected by the relationship line.

Figure 13:
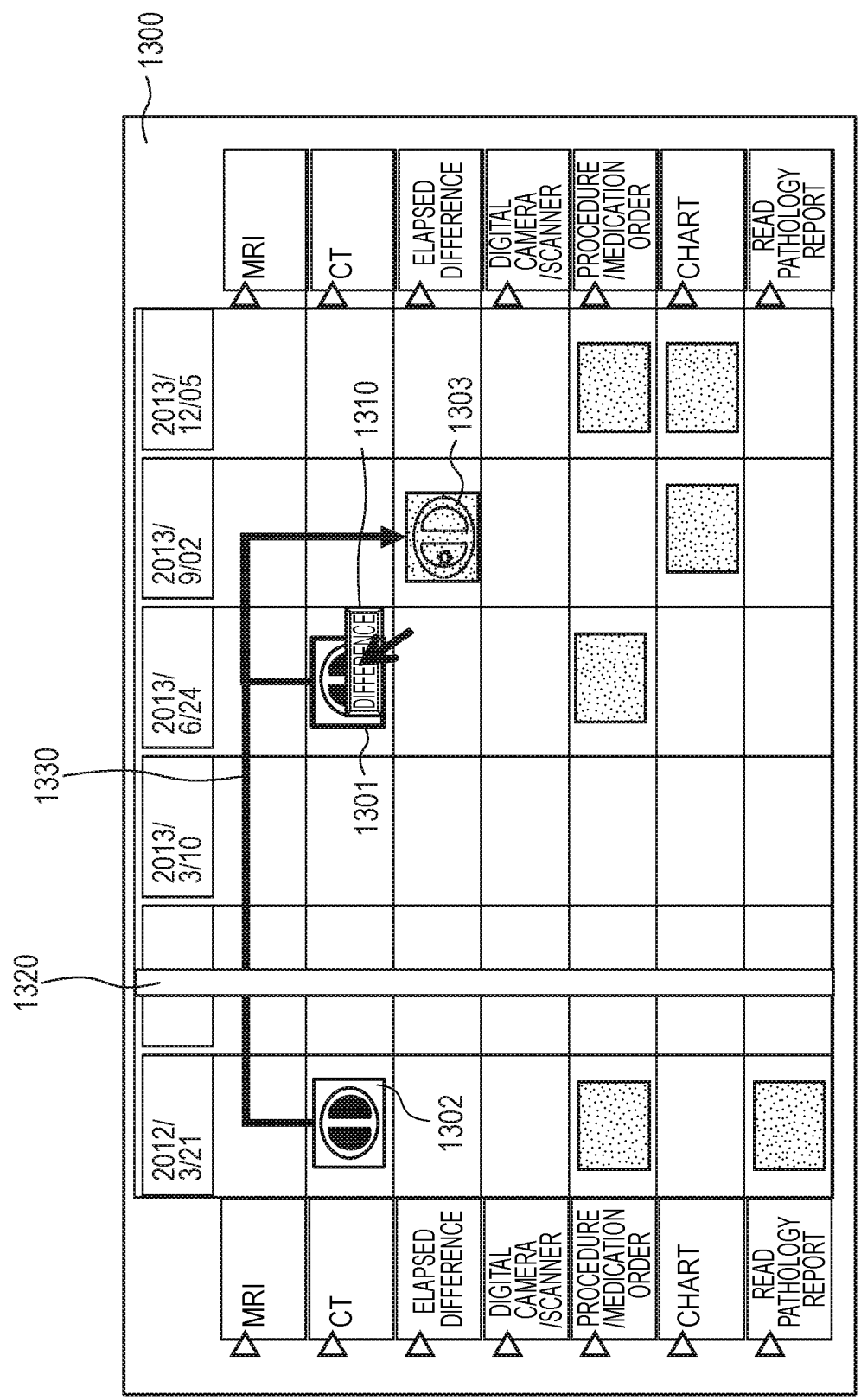
FIG. 13 is an explanatory diagram of a third embodiment.

FIG. 13 is a diagram illustrating an example of a display field 1300. Assume that a difference image corresponding to a thumbnail 1303 is produced from medical test images corresponding to thumbnails 1301 and 1302 displayed in the display field 1300. In addition, assume that the medical test image corresponding to the thumbnail 1301 is a base image, and the medical test image corresponding to the thumbnail 1302 is a floating image. In this case, the display processing unit 200 produces a relationship icon for the medical test image corresponding to the thumbnail 1301 and displays a relationship icon 1310 in the same cell as the cell of the thumbnail 1301. The date and time of a medical information item corresponding to the thumbnail 1302 is old. Therefore, at a time point of list display in S305, the thumbnail 1302 and the column including the thumbnail 1302 are assumed not to be displayed in the display field 1300.

Assume that, in this state, a user selects the relationship icon 1310 in S306. In this case, the display processing unit 200 adds, to the display field 1300, a column in which the thumbnail 1302 identified from the relationship icon 1310 is disposed, and then disposes the thumbnail 1302. Following the addition of the column of the thumbnail 1302, the display processing unit 200 removes a column that corresponds to a date later than the thumbnail 1302 and in which no thumbnails identified from the relationship icon 1310 are disposed. The display processing unit 200 provides, for example, a space 1320 to clearly display that the column corresponding to an in-between date is removed. The rest of the configuration and processes of the medical system according to the third embodiment are the same as the equivalent configuration and processes of the medical systems according to the other embodiments.

As seen from the above, in the third embodiment, when at least one of a plurality of thumbnails corresponding to medical information items having a relationship is hidden from the display field, the client apparatus 100 can add all of hidden thumbnails in the display field. The client apparatus 100 can further display a relationship line connecting all of the thumbnails corresponding to medical information items having a relationship and including the added thumbnail.

Figure 14:
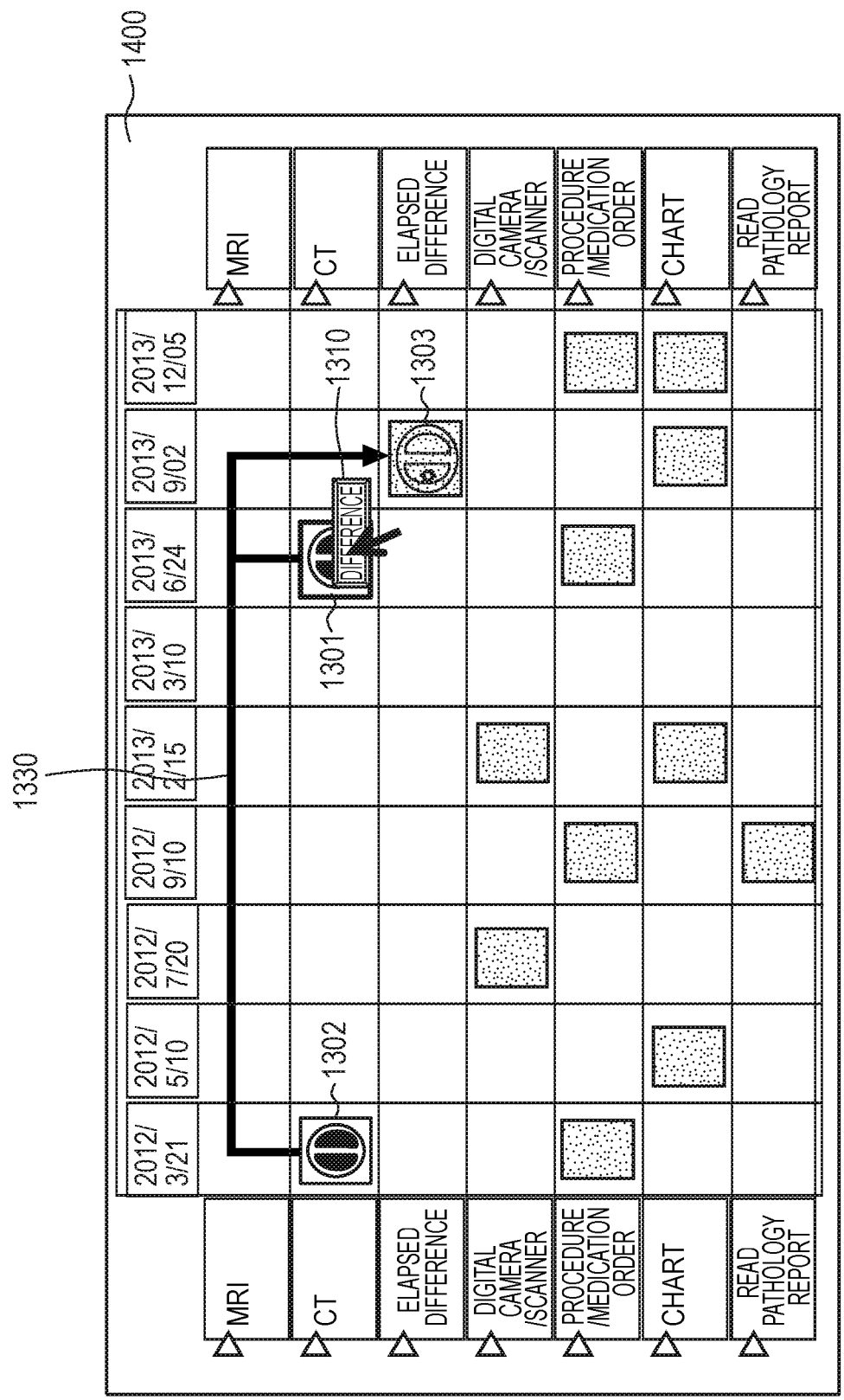
FIG. 14 is an explanatory diagram of a modification.

As to a modification of the third embodiment, the display processing unit 200 may increase the number of cells in the time-series direction rather than removing some of the columns of the display field. FIG. 14 is a diagram illustrating a display field corresponding to the display field 1300. In the display field 1400 illustrated in FIG. 14, the display processing unit 200 increases the number of cells in the time-series direction from six, the predetermined number, to nine, which allows a thumbnail 1302 connected by a relation line 1330 to be added to the display field 1400. In this case, the display processing unit 200 may display the thumbnails in a reduced form following the reduction of a cell size.

As seen from the above, exemplary embodiments of the present invention are described in detail, but the present invention is not limited to such specific embodiments, and various modifications and alterations may be made within the gist of the present invention as described and claimed herein.

OTHER EMBODIMENTS

The embodiments are described above in detail by way of example, but the present invention can include embodiments in the forms of, for example, systems, apparatuses, methods, programs, or recording media (storage media). Specifically, the present invention may be applied to a system constituted by a plurality of apparatuses (e.g., a host computer, interface apparatuses, imaging devices, and web applications) or may be applied to equipment constituted by a single apparatus.

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2017-114689, filed Jun. 9, 2017, which is hereby incorporated by reference herein in its entirety.

What is claimed is:

1. An information processing apparatus comprising:
at least one memory storing instructions; and
at least one processor that when executing the instructions, causes the information processing apparatus to function as:
a display control unit configured to display, in a case that it is determined whether a derived image generated on the basis of a first medical test image and a second medical test image which are included in a plurality of medical test images obtained by different medical tests, is or is not present, and it is determined that the derived image is present, an icon visually indicating that the derived image generated on the basis of the first medical test image and the second medical test image is present, on a display unit in conjunction with at least one of a thumbnail of the first medical test image and a thumbnail of the second medical test image,
wherein
the display control unit performs, when the icon is selected, such control as to display a display information item indicating a relationship between the first medical test image and the second medical test image, on the display unit.

2. The information processing apparatus according to claim 1, further comprising
a first determination unit configured to determine whether the first medical test image is associated with the second medical test image based on at least one of the medical test images and an additional information item of the medical test image.

3. The information processing apparatus according to claim 1, wherein the first medical test image and the second medical test image are the medical test images obtained by the different medical tests each of which are performed at different timings, and the derived image is a comparison image obtained by comparing the first medical test image with the second medical test image.

4. The information processing apparatus according to claim 3, wherein the comparison image is a subtraction image designating a difference between the first medical test image and the second medical test image.

5. The information processing apparatus according to claim 3, wherein the display control unit performs, when the icon is selected, such control as to display the display information item indicating a relationship between the first medical test image and the comparison image.

6. The information processing apparatus according to claim 1, wherein the display control unit performs, when the icon is selected, such control as to display the display information item indicating a relationship between the first medical test image, the second medical test image, and the derived image.

7. The information processing apparatus according to claim 1, wherein the display control unit performs, when a thumbnail of the derived image is selected, such control as to display the display information item indicating a relationship between the first medical test image and the derived image.

8. The information processing apparatus according to claim 1, wherein the display control unit performs, when a thumbnail of the derived image is selected, such control as to display the display information item indicating a relationship between the first medical test image, the second medical test image, and the derived image.

9. The information processing apparatus according to claim 1, wherein the display control unit
performs, in a case that it is determined that there are a plurality of derived images generated on the basis of the first medical test image, the second medical test image, and a third medical test image, such control as to display the icon visually indicating that the plurality of derived images generated on the basis of the first medical test image is present, in conjunction with a thumbnail of the first medical test image, and performs, when the icon is selected, such control as to display a relationship between the first medical test image, the second medical test image, and the third medical test image.

10. The information processing apparatus according to claim 1, wherein the display information item is a relationship line connecting the first medical test image and the second medical test image, to indicate a medical test image which is an original of the derived image.

11. The information processing apparatus according to claim 1, wherein the display information item is a text information item.

12. The information processing apparatus according to claim 1, wherein the display control unit performs, when a plurality of medical test images having different relationships with the first medical test image are presented, such control as to display a plurality of icons corresponding to a plurality of relationships, in conjunction with a thumbnail of the first medical test image.

13. The information processing apparatus according to claim 1, wherein the display control unit performs such control as to display a time-series display field in which a number of thumbnails displayable in a time-series direction is predetermined, and performs such control as to display thumbnails corresponding to the medical test image, in the display field in a time-series order in a form of a list.

14. The information processing apparatus according to claim 1, wherein
the display information item is a relationship line connecting a thumbnail of the first medical test image and a thumbnail of the second medical test image, and
the display control unit,
performs such control as to display a time-series display field in which a number of thumbnails displayable in a time-series direction is predetermined, and performs such control as to display thumbnails displayable in the display field, in the display field in a time-series order in a form of a list, and
removes, when the icon is selected in a case where at least one of a thumbnail corresponding to the first medical test image associated with the icon and a thumbnail corresponding to the second medical test image is not displayed in the display field, display of such one of the number of thumbnails as is displayed between the first medical test image and the second medical test image to perform such control as to display the thumbnail corresponding to the first medical test image and the thumbnail corresponding to the second medical test image in the display field simultaneously.

15. The information processing apparatus according to claim 13, wherein
the display control unit
performs such control as to display a time-series display field in which a number of thumbnails displayable in a time-series direction is predetermined, and performs such control as to display thumbnails displayable in the display field, in the display field in a time-series order in a form of a list, and
increases, when the icon is selected in a case where at least one of a thumbnail corresponding to the first medical test image associated with the icon and a thumbnail corresponding to the second medical test image is not displayed in the display field, the number of thumbnails displayable in the time-series direction to perform such control as to display a thumbnail corresponding to the first medical test image and a thumbnail corresponding to the second medical test image in the display field simultaneously.

16. A non-transitory tangible medium having recorded thereon a program for causing a computer to function as units of the information processing apparatus according to claim 1.

17. The information processing apparatus according to claim 1, wherein the icon is not displayed in a case that it is determined that the derived image is not present.

18. An information processing method performed by an information processing apparatus, the information processing method comprising:
displaying, in a case that it is determined whether a derived image generated on the basis of a first medical test image and a second medical test image which are included in a plurality of medical test images obtained by different medical tests, is or is not present, and it is determined that the derived image is present, an icon visually indicating that the derived image generated on the basis of the first medical test image and the second medical test image is present, on a display unit in conjunction with at least one of a thumbnail of the first medical test image and a thumbnail of the second medical test image; and
performing, when the icon is selected, such control as to display a display information item indicating a relationship between the first medical test image and the second medical test image, on the display unit.

19. An information processing apparatus comprising:
at least one memory storing instructions; and
at least one processor that when executing the instructions, causes the information processing apparatus to function as:
a display control unit configured to display, in a case that it is determined whether a derived image generated on the on the basis of a first medical test image and a second medical test image obtained by a medical test, is or is not present, and it is determined that the derived image is present, an icon visually indicating that the derived image generated on the basis of the first medical test image and the second medical test image is present, on a display unit in conjunction with at least one of a thumbnail of the first medical test image and a thumbnail of the second medical test image,
wherein
the display control unit performs, when the icon is selected, such control as to display a display information item indicating a relationship between the derived image and at least one of the first medical test image and the second medical test image, on the display unit.

20. An information processing apparatus comprising:
at least one memory storing instructions; and
at least one processor that when executing the instructions, causes the information processing apparatus to function as:
a display control unit configured to display, in a case that it is determined whether a subtraction image designating a difference between a first medical test image and a second medical test image which are included in a plurality of medical test images obtained by different medical tests, is or is not present, and it is determined that the subtraction image is present, an icon visually indicating that the subtraction image which designates the difference between the first medical test image and the second medical test image is present, on a display unit in conjunction with at least one of a thumbnail of the first medical test image and a thumbnail of the second medical test image.

\* \* \* \* \*